(12) United States Patent
Saxena et al.

(10) Patent No.: US 8,461,980 B2
(45) Date of Patent: Jun. 11, 2013

(54) WELLBEING TRANSPONDER SYSTEM

(75) Inventors: Narothum Saxena, Hoffman Estates, IL (US); Michael Irizarry, Barrington Hills, IL (US); Ravideep Bhatia, West Dundee, IL (US)

(73) Assignee: United States Cellular Corporation, Chicago, IL (US)

( * ) Notice: Subject to any disclaimer, the term of this patent is extended or adjusted under 35 U.S.C. 154(b) by 228 days.

(21) Appl. No.: 12/859,532

(22) Filed: Aug. 19, 2010

(65) Prior Publication Data

US 2012/0044069 A1  Feb. 23, 2012

(51) Int. Cl.
*G08B 1/08* (2006.01)

(52) U.S. Cl.
USPC ............ 340/539.12; 340/539.13; 340/539.26; 340/573.1; 340/573.4; 340/5.6; 340/7.1; 340/10.1; 340/10.4

(58) Field of Classification Search
USPC .............. 340/539.12, 539.13, 539.26, 573.1, 340/573.4, 5.6, 7.1, 10.1, 10.4
See application file for complete search history.

(56) References Cited

U.S. PATENT DOCUMENTS

| | | | |
|---|---|---|---|
| 6,100,806 A * | 8/2000 | Gaukel | 340/573.4 |
| 6,847,892 B2 * | 1/2005 | Zhou et al. | 701/408 |
| 8,265,907 B2 * | 9/2012 | Nanikashvili et al. | 702/188 |

* cited by examiner

*Primary Examiner* — Tai T Nguyen
(74) *Attorney, Agent, or Firm* — Leydig, Voit & Mayer, Ltd.

(57) ABSTRACT

The described system and method enable user health monitoring and alerting by providing an arm-mounted sensor wirelessly linked to a wrist-mounted transponder, although the wrist-mounted transponder may be omitted in favor of a user-carried cellular device. In either embodiment of the invention, a remote server is included to receive user health data and alerts, and to log received data and, when necessary, to alert health service providers. Health service providers may include physicians and emergency services providers.

17 Claims, 5 Drawing Sheets

WELLBEING TRANSPONDER SYSTEM

TECHNICAL FIELD

This patent disclosure relates generally to health and wellbeing monitoring and, more particularly to a method and system for monitoring user wellbeing via a wristband and associated communication system and application.

BACKGROUND

Although health and health-related parameters are of substantial importance to many people, very few people are actually adept at interpreting and properly utilizing such data to improve or preserve their health and well-being. Moreover, even for those individuals with enough knowledge and experience to properly utilize the data, it is difficult for the typical user to collect such data during exercise or other busy periods. Although certain body worn transponder systems may have been attempted, the inventors are not aware of any such system that has fully solved the problems noted above.

It will be appreciated that this brief background description has been created by the inventors to aid the reader, and represents concepts known to the inventors. It is not a discussion of, nor reference to, prior art, nor is this section intended to imply that any of the indicated problems were themselves appreciated in the art. Terms such as "may have" are intended to identify speculation and not to signify the actual existence of any particular system. While the principles described herein can, in some regards and embodiments, avoid the problems described, it will be appreciated that the scope of the protected innovation is defined by the attached claims, and not by the ability of the claimed invention to solve any specific problem noted herein.

SUMMARY

The described system and method facilitate user health monitoring and alerting. To this end, the system includes, in an embodiment, an arm-mounted sensor wirelessly linked to a wrist-mounted transponder. In an alternative embodiment of the invention, the wrist-mounted transponder is omitted in favor of a user-carried cellular device. In any case, a remote server is included to receive user health data and alerts, and to log received data and, if necessary, to alert health service providers, e.g., a physician or emergency services provider, regarding a detected user health issue.

Further and alternative aspects and features of the disclosed principles will be appreciated from the following detailed description and the accompanying drawings, of which:

DETAILED DESCRIPTION

In overview, this disclosure relates to a system and architecture for monitoring user health parameters and selectively conveying the parameters or a derivative thereof to a remote recipient in conjunction with further off-board processing by an intermediate processor to provide enhanced health monitoring and response for the user. With reference to the basic elements of the system, the system in an embodiment includes an arm-mounted data collection band in wireless communication with a wrist-mounted transponder unit. The transponder unit collects data from the data collection band and processes the data for further transmission to a remote recipient. The remote recipient may be a health service provider such as a physician associated with the user, or, when warranted, an emergency service provider.

Figure 1:
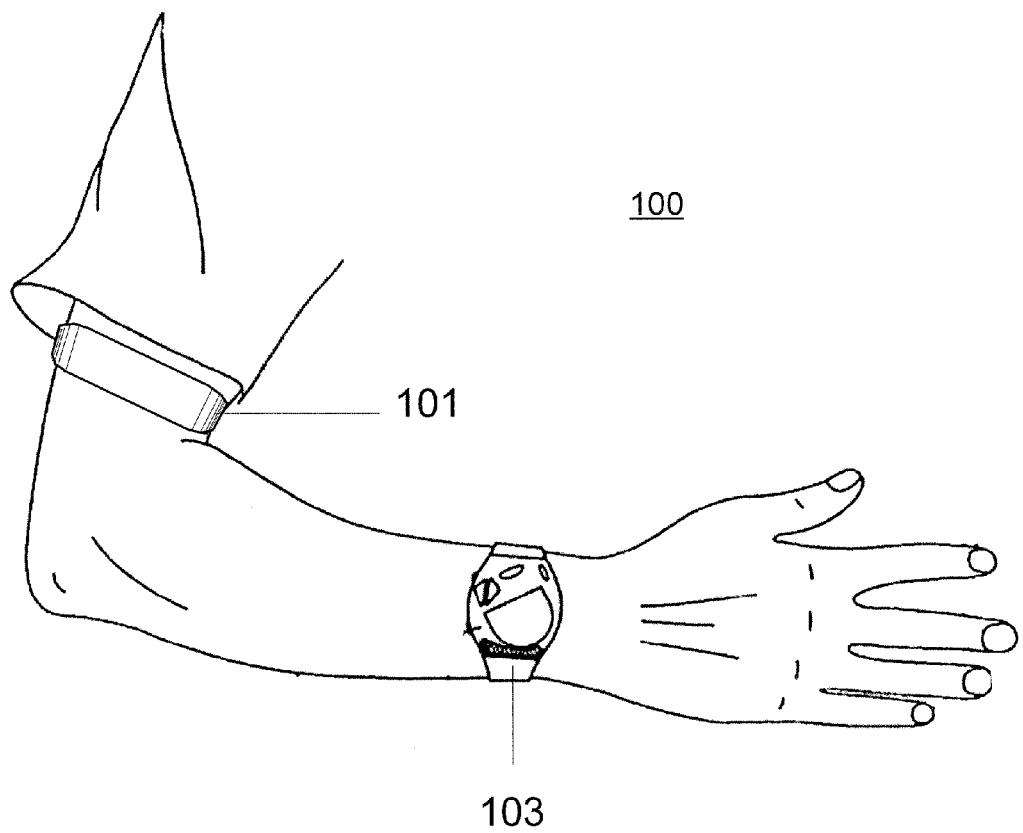
FIG. 1 is a simplified environmental schematic showing an arm-mounted band and wrist-mounted transponder within which embodiments of the described system may be implemented.

With this overview in mind, specific details of the described principles and system will now be discussed. FIG. 1 is a simplified environmental schematic 100 showing an arm-mounted data collection band 101 and a wrist-mounted transponder 103 within which embodiments of the described system may be implemented. The arm-mounted data collection band 101 may be of any suitable type known in the art, and may be capable of collecting data including, for example, heart rate, respiration rate, temperature, etc. The arm-mounted data collection band 101 communicates wirelessly with the wrist-mounted transponder 103. As will be discussed in greater detail below, the wrist-mounted transponder 103 is configured to convey the collected parameters or a derivative thereof to an intermediate processor (not shown in FIG. 1) for further off-board processing, and from there to a remote recipient, i.e., a physician or emergency service provider.

Figure 2:
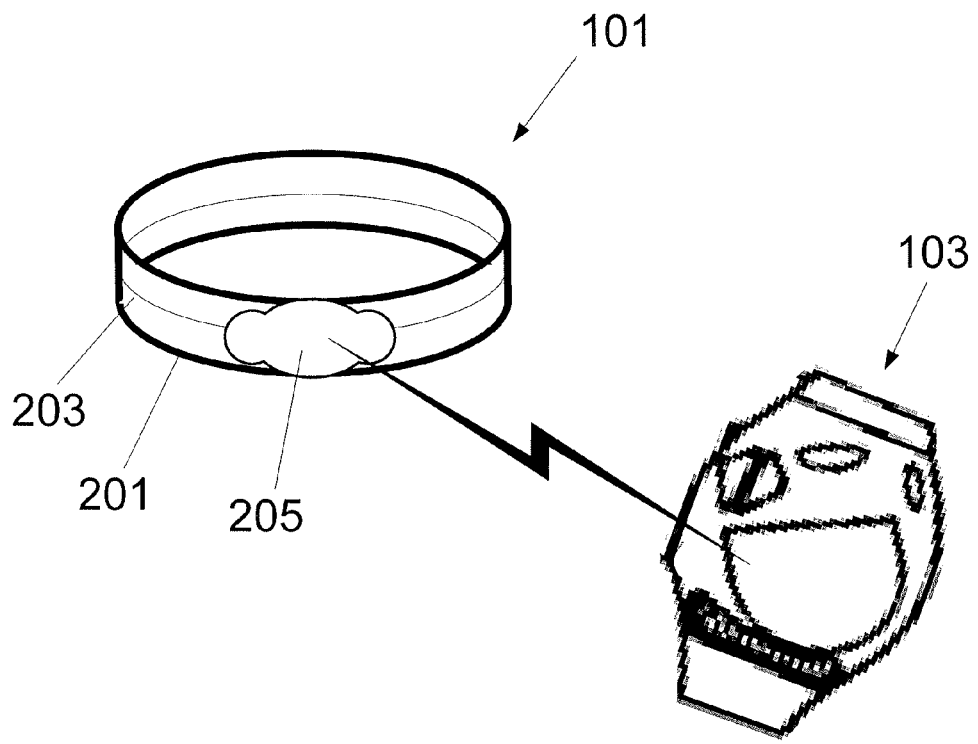
FIG. 2 is a more detailed schematic view of the in accordance with the described principles.

Referring now to FIG. 2, wherein like reference numerals refer to like elements, the system is described in greater detail. As can be seen, the arm-mounted data collection band 101 includes a body portion 201 that forms the majority of the device and holds the device to the user while also holding the other portions of the arm-mounted data collection band 101. Other portions of the device include a sensor portion 203, illustrated as a wire for the sake of simplicity but able to have any suitable configuration as will be appreciated by those of skill in the art. The arm-mounted data collection band 101 also includes a sender 205 configured to receive data from the sensor portion 203 of the arm-mounted data collection band 101 and to convey the collected data to the wrist-mounted transponder 103.

The communications between the arm-mounted data collection band 101 and the wrist-mounted transponder 103 are wireless, and may be via any suitable protocol or system, e.g., Bluetooth, ZigBee, etc. ZigBee is particularly useful since it is specifically adapted for use in small, low-power digital radios based on the IEEE 802.15.4-2003 standard for wireless personal area networks. ZigBee's low data rate is not a hindrance in the present application, and ZigBee's low power draw and enhanced battery life are quite beneficial. Thus for example, the arm-mounted data collection band 101 may collect data related to user heart rate by counting pulses over a period of time, e.g., via a pressure transponder or otherwise. The arm-mounted data collection band 101 then sends the collected data, e.g., via ZigBee, to the wrist-mounted transponder 103.

Figure 3:
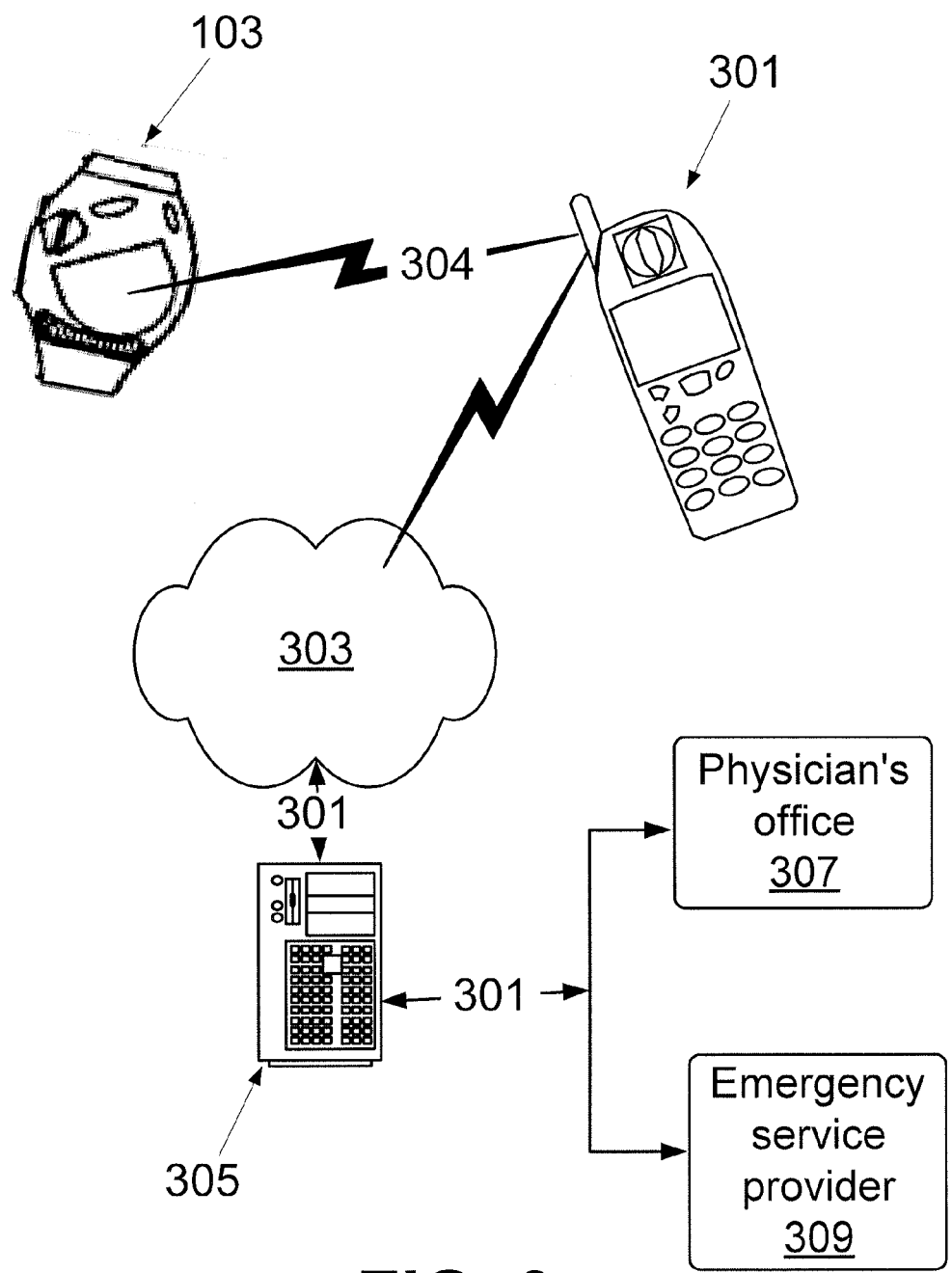
FIG. 3 is a detailed schematic of data stream elements in the progression of the data through the described system.

Upon receiving the collected data of whatever type from the arm-mounted data collection band 101, the wrist-mounted transponder 103 may process the data as needed or desired, e.g., converting a stream of pulse-per-minute readings to a pulse average, and then transmits the data onward. The data stream elements of the continuing progression of the data are shown in FIG. 3.

The wrist-mounted transponder 103 is in wireless communication with a user communication device 301, such as a cell phone or other device capable of communicating wirelessly with a network access point, directly or indirectly. The wireless channel 304 may be any suitable channel, e.g., Bluetooth, ZigBee, etc. The receipt of the signal at the user communication device 301 from the wrist-mounted transponder 103 serves to trigger instantiation of an application running on the user communication device 301. The application initiates communication from the user communication device 301 to a server 305 via a wireless network 303 such as a cellular network or otherwise. In particular, the wireless network 303 may be a CDMA, W-CDMA, GSM, LTE, WiFi, and so on.

An application or website hosted at the server 305 is then activated to analyze the received data for possible further action. In particular, if the data indicates an unhealthy condition of which the user may be unaware, such as high blood pressure, arrhythmia, missed heart beats, etc., the application running on the server 305 causes a communication to be sent to an appropriate health care provider, e.g., the user's registered physician 307. The communication from the server 305 to the user's registered physician 307 may be by any suitable means including wired and wireless communications as well as combinations of the two means.

Similarly, if the received data indicates a dangerous current health condition such as dangerously high blood pressure, imminent heart attack, impending stroke, etc., the application running on the server 305 causes a communication to be sent to an appropriate emergency health care provider, e.g., a local (to the user) hospital emergency service provider 309. As with the less urgent case, the communication from the server 305 to the emergency service provider 309 may be by any suitable means, whether wired, wireless or a combination of the two.

Before turning to the process flow of an embodiment of the invention, a brief discussion of the data entry aspects of the system is in order. As will be readily appreciated, due to size and weight constraints, the arm-mounted data collection band 101 and the wrist-mounted transponder 103 have limited user interface capabilities, and are generally not suitable for data entry, i.e., to enter user health data, program data, etc. However, the user communication device 301, which may be a cell phone or similar device, may have suitable or even extensive data entry capabilities, e.g., a keyboard or other entry device and a screen or other GUI device.

Thus, as part of initially setting up the system, and to make changes to data or programming during use of the system, the user may employ the user communication device 301 to edit user data, i.e., setting heart rate thresholds, weight, etc., as well as to change program parameters such as physician and emergency service contact information. The parameters and data used by the program, including historical user data, may be stored on the user communication device 301, the server 307, or both.

In an alternative embodiment of the invention, the user employs a personal computer or other networked computing device in conjunction with the server 307 to alter program data and parameters via the website hosted by the server 307. As with the aforementioned embodiment of the invention, program data and parameters, however entered or collected, may be stored at either the user communication device 301 or the server 307.

Figure 4:
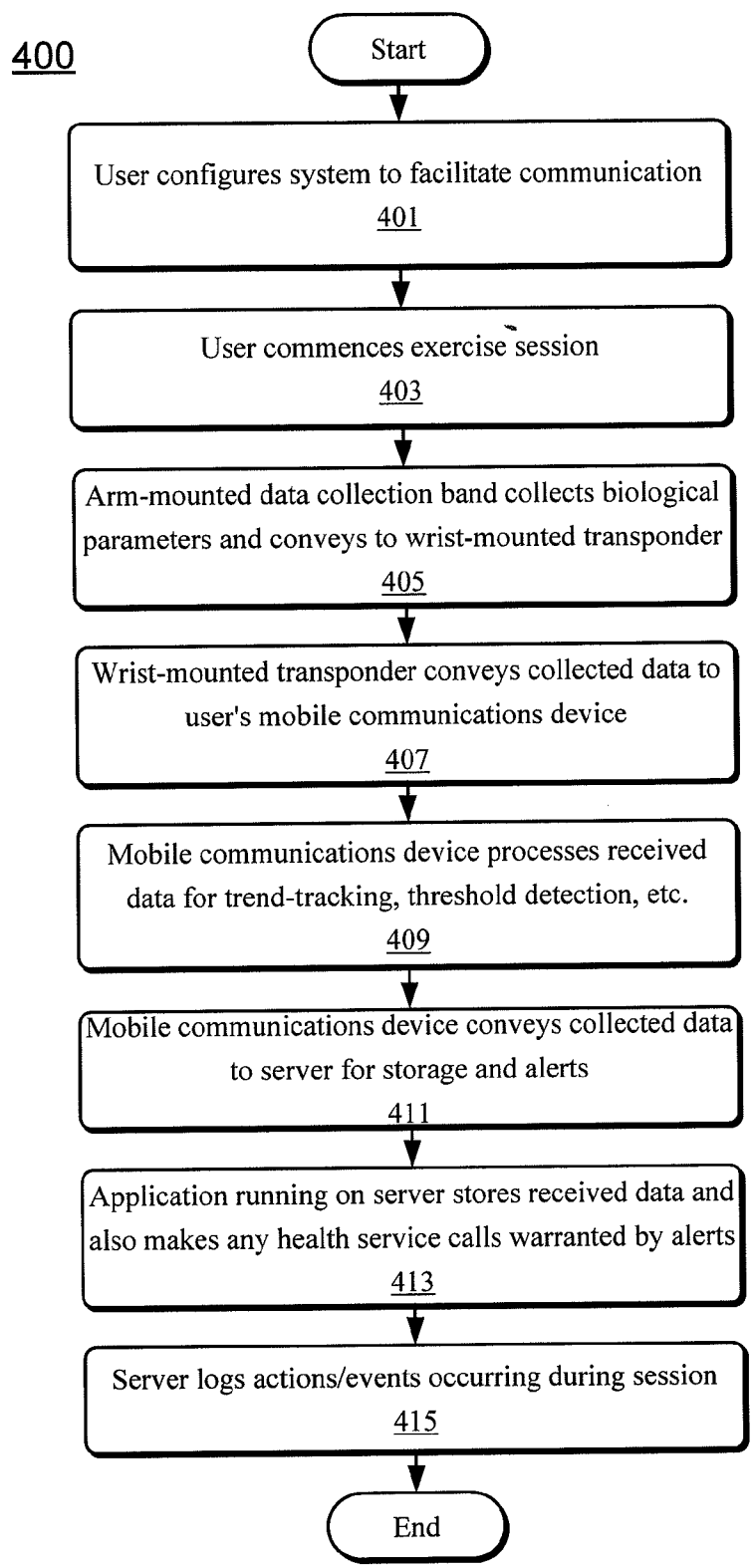
FIG. 4 is a flow chart showing an exemplary process flow for using the described system to facilitate user health maintenance and alerting in accordance with the described principles.

The flow chart of FIG. 4 illustrates a process 400 of using the described system for user health maintenance and alerting. At stage 401 of the process 400, the user sets up the system to facilitate communication as described above. Thus, for example, in an embodiment of the invention, the user subscribes via the server 307 to maintain and communicate personal health data, including providing user health information (weight, height, age, known conditions, allergies, etc.) and contact information (e.g., telephone numbers and ID for physician of record and emergency service provider). The user may also which health parameters to observe, although in an embodiment of the invention, any parameter detected by the arm-mounted data collection band 101 is tracked. Available parameters include, for example, calories used, heart rate, blood pressure, miles/km traveled, time elapsed while exercising, and other parameters as appropriate for a given implementation. In an embodiment of the invention, the user's position is also tracked, e.g., to assist with locating health service providers or otherwise. The location may be determined via the user's mobile communications device 301, for example, via GPS, triangulation, or otherwise.

At stage 403 of the process 400, the user having already configured the system as desired, the user at some point starts a session of exercise. The commencement of the session may be signaled to the system entities by a signal produced when the arm-mounted data collection band 101 is turned on.

As the user exercises, the arm-mounted data collection band 101 collects certain biological parameters at stage 405 and conveys them to the wrist-mounted transponder 103. The wrist-mounted transponder 103 in turn conveys the collected data, as-is or in a transformed state, to the user's mobile communications device 301 at stage 407.

In an embodiment of the invention, the mobile communications device 301, via the application running thereon, further processes the received data for purposes of trend-tracking, threshold detection, and so on at stage 409. For example, the mobile communications device 301 may monitor whether the user's heart rate exceeds a predetermined threshold, whether the user's blood pressure is too high or too low, etc. At stage 411, the mobile communications device 301 conveys the collected data to the server 307 for storage, along with any appropriate health alerts. The application running on the server stores the received data at stage 413, and also makes any health service calls as warranted by any alerts sent by the mobile communications device 301.

At stage 415, the server 307 logs the actions taken and events occurring during the session, i.e., alerts created and service calls made. The log may be exhaustive, or may include a predetermined number of most recent events, alerts, and/or service calls.

Figure 5:
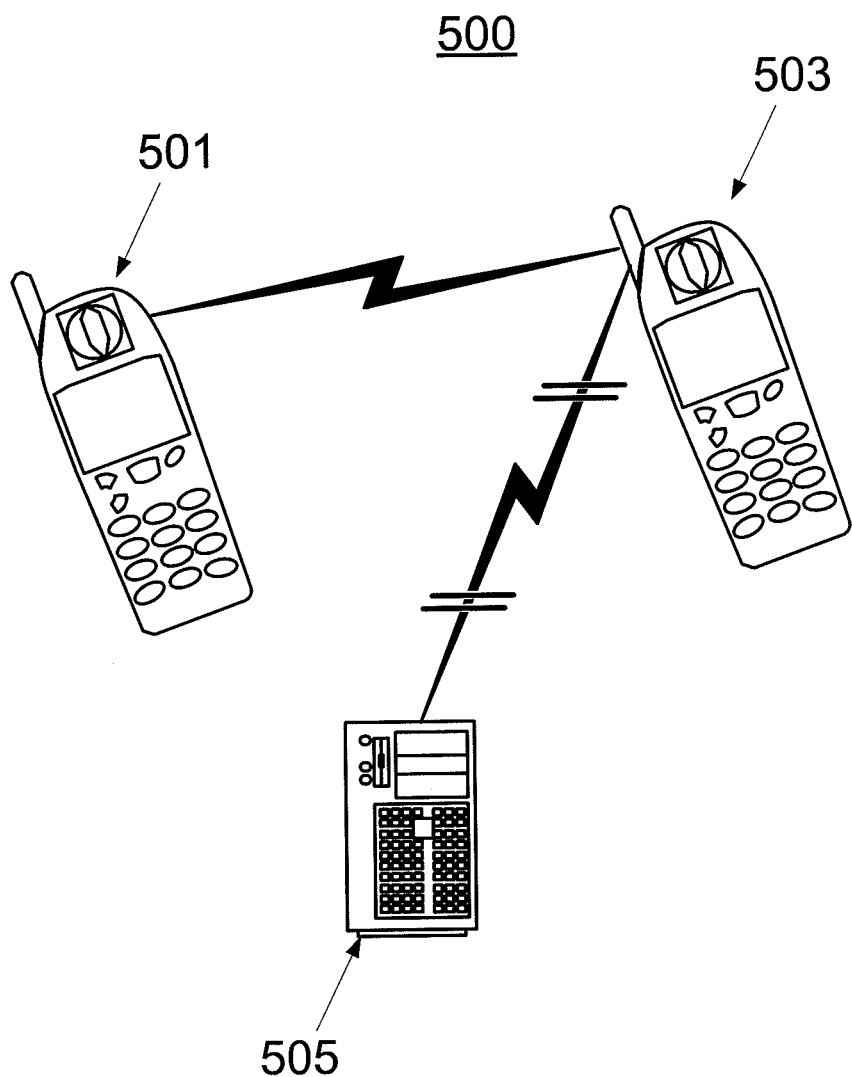
FIG. 5 is a schematic diagram illustrating an alternative architecture within which the described principles may be used.

An alternative architecture 500 within which the described principles may be used is illustrated in the schematic diagram of FIG. 5. In particular, a first user device 501 is maintained on the user and collects health parameters directly or indirectly, e.g., via an arm-mounted collection device such as arm-mounted data collection band 101. The device on the user then conveys the collected data, in raw or processed form, via local wireless facilities such as Bluetooth, to another user device 503. The second user device 503 is a cellular device or other device capable of long range wireless communication, and the second device conveys the received data to a server 505, similar to server 307. The server treats the received information, in terms of event, alerts, and logging, as described above with respect to FIG. 3.

Given the foregoing description, it will be appreciated that the invention provides a health data tracking and action system that improves user health safety and convenience. However, it will also be appreciated that the described principles are susceptible to various changes and modification without departing from the true scope of the invention.

Thus, although it will be appreciated that the foregoing description provides useful examples of the disclosed system and technique, it should be appreciated that other implementations of the disclosed principles will differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for the features of interest, but not to exclude such from the scope of the disclosure entirely unless otherwise specifically indicated.

Recitation of ranges of values herein are merely intended to serve as a shorthand method of referring individually to each separate value falling within the range, unless otherwise indicated herein, and each separate value is incorporated into the specification as if it were individually recited herein.

We claim:

1. A system for remotely monitoring user health status, the system comprising:
   a first user-borne data collection module configured to:
      collect values of one or more biological parameters from a user, and transmit a representation of the values of the one or more biological parameters;
   a second user-borne data collection module configured to:
      receive the representation of the collected values,
      process the representation of the collected values to render a processed representation of the collected values, and
      wirelessly transmit, via a wireless channel, the processed representation of the collected values; and
   a mobile wireless communication device associated with the user, the mobile wireless communication device being configured to:
      receive, via the wireless channel, the processed representation of the collected values, and
      forward, via a mobile wireless network connection, the processed representation of the collected values to a server coupled to a data network; and
   a group of networked health care provider devices communicatively coupled to the server, the group of networked health care provider devices comprising at least:
      a first networked provider device associated with a registered physician for the user, and
      a second networked provider device associated with an emergency health care provider;
   wherein the server is configured to:
      receive the processed representation of the collected values,
      analyze the processed representation of the collected values to determine a health condition of the user, and
      selectively convey, based upon the health condition of the user, a communication to at least one of the group of networked health care provider devices.

2. The system of claim 1, wherein the server is configured to convey the communication to an emergency service provider when the health condition of the user indicates a dangerous current health condition.

3. The system of claim 1, wherein the first user-borne data collection module comprises an arm-mounted data collection band.

4. The system of claim 1, wherein the second user-borne data collection module comprises a wrist-mounted transponder.

5. The system of claim 1, wherein the one or more biological parameters include at least one parameter selected from the group consisting of user heart rate, user respiration rate, user temperature, user blood pressure and user calories burned.

6. The system of claim 1, wherein communications between the first user-borne data collection module and the second user-borne data collection module are executed via a short range wireless protocol.

7. The system of claim 6, wherein the short range wireless protocol is one of the group consisting of: BLUETOOTH and ZIGBEE.

8. The system of claim 1, wherein the second user-borne data collection module is configured to convert, during processing, the representation of the collected values to another form.

9. The system of claim 1, wherein the mobile wireless communication device comprises a cell phone associated with the user.

10. The system of claim 1, wherein the mobile wireless communication device is configured to communicate with the server via an intermediate data network linked to the server.

11. The system of claim 10, wherein the mobile wireless network connection incorporates a wireless protocol taken from the group consisting of: CDMA, W-CDMA, GSM, LTE, WiFi and WiMax.

12. The system of claim 10, wherein the mobile wireless communication device is further configured to determine a geographic position of the user, and to communicate a geographic position data value, corresponding to the geographic position, to the server.

13. The system of claim 12, wherein the server is further configured to convey the geographic position data value to at least one of the group of networked health care provider devices.

14. The system of claim 1, wherein the mobile wireless communication device is configured to allow the user to edit user data associated with the user and to enter physician and emergency service contact information.

15. The system for monitoring user according to claim 1, wherein the mobile wireless communication device is further configured to:
   generate historical user health data, and
   store historical user health data.

16. The system of claim 1, wherein the server is further configured to receive, from a networked computing device, user health information, physician contact information, and emergency service contact information.

17. The system of claim 1, wherein the second user-borne data collection module collects data from multiple sensors attached to the user.

* * * * *